United States Patent [19]

Ekwall

[11] Patent Number: 4,827,934

[45] Date of Patent: May 9, 1989

[54] SENSING MARGIN DETECTORS FOR IMPLANTABLE ELECTROMEDICAL DEVICES

[75] Inventor: Christer Ekwall, Spånga, Sweden

[73] Assignee: Siemens-Pacesetter, Inc., Sylmar, Calif.

[21] Appl. No.: 114,327

[22] Filed: Oct. 27, 1987

[51] Int. Cl.[4] .............................................. A61D 1/36
[52] U.S. Cl. ...................... 128/419 PG; 128/419 PT; 128/703
[58] Field of Search ................. 128/419 PG, 419 PT, 128/421, 422, 703, 695, 697

[56] References Cited

U.S. PATENT DOCUMENTS

| | | | |
|---|---|---|---|
| 4,332,256 | 6/1982 | Brownlee et al. | 128/419 PT |
| 4,476,869 | 10/1984 | Bihn | 128/419 PT |
| 4,516,579 | 5/1985 | Irnich | 128/419 PG |
| 4,640,285 | 2/1987 | DeCote, Jr. et al. | 128/419 PT |
| 4,664,116 | 5/1987 | Shaya et al. | 128/419 PT |
| 4,708,142 | 11/1987 | DeCote, Jr. | 128/419 PT |
| 4,712,555 | 12/1987 | Thornander et al. | 128/419 PG |
| 4,729,376 | 3/1988 | DeCote, Jr. | 128/419 PT |
| 4,766,902 | 8/1988 | Schroeppel | 128/419 PG |
| 4,768,511 | 9/1988 | DeCote, Jr. | 128/419 PG |

OTHER PUBLICATIONS

Stimulated Heart Interval Measurement, Adaptive Pacer And Method of Operation, Inventors: Hans T. Thornander; Jason A. Sholder; and James R. Thacker, International Filing Date: Oct. 11, 1985, Priority Date & Country: Mar. 27, 1985 (U.S.).

Primary Examiner—Leo P. Picard
Assistant Examiner—Jessica Harrison
Attorney, Agent, or Firm—Henry M. Bissell; Bryant R. Gold; Leslie S. Miller

[57] ABSTRACT

Circuitry for quantitatively determining the level of processed heart signals relative to actual sensing sensitivity level (threshold) in an implantable pacemaker. The measurement is useful for adjusting the settable threshold, polarity, filtering or amplification parameter settings for safe operation and noise rejection of the pacemaker.

20 Claims, 2 Drawing Sheets

SENSING MARGIN DETECTORS FOR IMPLANTABLE ELECTROMEDICAL DEVICES

This invention relates to implantable electromedical devices and, more particularly, to circuitry thereof for determining the sensing margin of a sensed event detector and adjusting signal detecting threshold level to promote safe operation of the device.

BACKGROUND OF THE INVENTION

The technology of cardiac pacemakers has developed to a high level of sophistication of system performance. The current generation of cardiac pacemakers may incorporate microprocessors and related circuitry to sense and stimulate heart activity under a variety of physiological conditions. These pacemakers are programmed to control the heart in correcting or compensating for various heart abnormalities which may be encountered in individual patients. A detailed description of modern cardiac pacemaker technology is set forth in International Application No. PCT/US85/02010, entitled Stimulated Heart Interval Measurement, Adaptive Pacer and Method of Operation, assigned to the assignee hereof. The disclosure of that application is incorporated herein by reference.

In order to efficiently perform its function as a pump, the heart must maintain a natural AV synchrony. The term "AV synchrony" relates to the sequential timing relationship that exists between the contractions of the atria and the ventricles. In a given heart cycle or beat, these contractions are typically manifest or measured by sensing electrical signals or waves that are attendant with the depolarization of heart tissue, which depolarization immediately precedes (and for most purposes can be considered concurrent with) the contraction of the cardiac tissue. These signals or waves can be viewed on an electrocardiogram and include a P-wave, representing the depolarization of the atria; the QRS wave (sometimes referred to as an R-wave, the predominant wave of the group), representing the depolarization of the ventricles; and the T-wave, representing the repolarization of the ventricles. (It is noted that the atria also are repolarized, but the main reason why atrial repolarization is not seen is that the muscular mass of the atrium is so much smaller, compared to the ventrical.)

Thus, it is the P-QRS-T cycle of waves that represents the natrual AV synchrony of the heart. These waves, including the time relationships that exist therebetween, are carefully studied and monitored through conventional surface or non-intracardial ECG techniques whenever the operation of the heart is being examined.

Initiation of the cardiac cycle normally begins with depolarization of the sinoatrial (SA) node. This specialized structure is located in the upper portion of the right atrium wall. The SA node depolarizes spontaneously at an intrinsic rate of a little better than once each second (typically about 72 beats per minute). The rate of depolarization and, therefore, the heart rate are influenced by various physical factors, such as nerval (parasympaticus) or hormone stinulation. These factors increase heart contraction rate from levels of 50 beats per minute at rest up to 180 beats per minute under work load.

Optimally, in a normal cardiac cycle and in response to the initiating SA depolarization, the atrium contracts and forces the blood that has accumulated therein into the ventricle. A short time later (a time sufficient to allow the bulk of the blood in the atrium to flow through the one-way valve into the ventricle), the ventricle contracts, forcing the blood out of the ventricle to body tissue. A typical time interval between contraction of the atrium and contraction of the ventricle might be 120 ms; a typical time interval between contraction of the ventricle and the next contraction of the atrium might be 650 ms. Thus, it is an atrial contraction (A), followed a relatively short time thereafter by a ventrical contraction (V), followed a relatively long time thereafter by the next atrial contraction, that produces the desired AV synchrony. Where AV synchrony exists, the heart functions very efficiently as a pump in delivering life-sustaining blood to body tissue; where AV synchrony is absent, the heart functions as an inefficient pump (largely because the ventricle is contracting when it is not filled with blood).

Multiple-mode, demand-type, cardiac pacemakers are designed, insofar as is possible, to maintain an AV synchrony for damaged or diseased hearts that are unable to do so on their own. A demand-type pacemakers is one that provides a stimulation pulse only when the heart fails to produce a natural depolarization on its own within a prescribed escape interval. In a dual chamber pacemaker, this is realized by placing electrodes in both the right atrium and right ventricle of the heart. These electrodes are coupled through intravenous and/or epicardial leads to sense amplifiers housed in an implanted pacemaker. Electrical activity occurring in these chambers can thus be sensed. When electrical activity is sensed, the pacemaker assumes that a depolarization or contraction of the indicated chamber has occurred. If no electrical activity is sensed within a prescribed time interval, typically referred to as an atrial or ventricular escape interval, then a pulse generator, also housed within the pacemaker housing, generates a stimulation pulse that is delivered to the indicated chamber, usually via the same lead or electrode as is used for sensing. This stimulation pulse causes or forces the desired depolarization and contraction of the indicated chamber to occur. Hence, by first sensing whether a natural depolarization occurs in each chamber, and by second stimulating at controlled time intervals each chamber with an external stimulation pulse in the absence of a natural depolarization, the AV synchrony of the heart can be maintained. Thus, with a demand pacer, the heart will either beat on its own (without stimulation from the pacemaker) at a rate that is at least just slightly faster than the stimulation rate defined by the escape interval, or the heart will be stimulated by the pacer at a rate controlled by the escape interval. The stimulation rate provided by the pacemaker is typically referred to as the "programmed rate".

Unfortunately, there are many operating constraints and conditions of the heart that complicate the operation of a demand-type pacemaker. For example, there are certain time periods following a depolarization of cardiac tissue (prior to repolarization) when the application of an external electrical impulse is ineffective---that is, it serves no useful purpose, and thus represents an unneeded expenditure of the pacemaker's limited energy. Therefore the application of stimulation pulses during these time period is to be avoided.

Rate responsive pacemakers employ some type of physiological sensor for sensing a change in the metabolic needs of a patient. This sensed change, in turn, is used to adjust the rate at which stimulation pulses are delivered to the heart of the patient by the pacemaker. Thus, as the metabolic needs of the patient increase—indicating a need for the heart to beat faster—the rate at which the pacemaker stimulates the heart is increased as a function of this sensed increase in metabolic need. As the metabolic needs of the patient decrease—indicating a need for the heart to beat slower—the rate at which the pacemaker stimulates the heart is correspondingly decreased.

In a demand pacer, the physiological sensor (which may be one of numerous types) adjusts the pacing rate by adjusting the escape interval of the pacer. As the escape interval is thus adjusted as a function of sensed physiological need, the rate at which stimulation pulses are provided to the heart—and hence the heart rate—is correspondingly varied as a function of sensed physiological need.

Rate-responsive demand pacers are typically single chamber pacers that sense and stimulate in the ventricle (VVI) at a rate determined by the particular phsiological sensor used. Patients who are candidates for rate-responsive pacing usually include patients exhibiting partial or complete heart block. When heart block exists, the ventricle does not consistently follow the atrium, and the needed and desired AV synchrony is lost. A rate-responsive pacer advantageously allows the ventricle to be stimulated at a rate commensurate with the sensed physiological need despite the existence of heart blockage.

Fully automatic, dual chamber pacemakers (DDD) are capable of sensing and pacing in both the atrium and ventricle. Such a pacemaker combines the feature of AV sequential pacing with stimulation of the ventricle in response to atrial sensing. Such a pacemaker may also provide stimulation at a pre-programmed minimum rate.

It is customary in such pacemakers to incorporate an input signal sensing detector which may be used to modify or inhibit pacemaker reaction to a sensed physiological signal. For example, in the pacemaker, the electrophysiological signal from a heart contraction is received, amplified and processed in order to suppress noise and other extraneous signals. The resulting signal is fed into the input sensing detector. The output from the sensing detector may be used to inhibit pacemaker stimulation when normal heart activity is detected (VVI) or to synchronize pacemaker stimulation to the heart activity (DDD), depending on pacemaker operation mode.

In these applications, a certain minimal amount of input signal energy (signal level) is required to activate the detector. The sensing detector activating level (sensing threshold) may be fixed—i.e., preset—or adjustable (programmable). In the latter case, the adjustability is usually selected in discrete steps. For whatever threshold level is determined, an output signal from the sensing detector is an indication that the threshold has been exceeded by a processed heart signal. However, the amount of energy or signal extent above the threshold cannot usually be determined in presently known systems.

The extent by which the input signal exceeds the threshold is defined as the "sensing margin". If the input signal exceeds the threshold significantly, the sensing margin is defined as high. If the input signal just reaches or barely exceeds the detector threshold level, the sensing margin is low or zero. For a given level of input signal to the sensing detector, sensing margin is determined by adjusting the detector threshold level.

In order to assure safe operation of an implanted pacemaker, it is important to establish a correct sensitivity setting or threshold level. The proper sensitivity setting of the pacemaker may be affected by a number of factors. For example, the sensing properties of the pacemaker as implanted may be different from those of the measuring equipment preliminarily used to determine sensitivity level. Also, the sensing properties of the pacemaker may be changed after implantation by programming of the device. There may also be a change in the sensed signal property after implantation as a result of physiological changes over time. It is therefore considered important to to be able to determine the optimum threshold level setting of the sensing detector for the actual implanted pacemaker with its actual sensing properties and control settings. An implantable pacemaker having the capability of determining the sensing margin and adjusting sensing detector threshold to an optimum level after implantation will significantly increase the safety and ease of use of the pacing system.

In the field of pacemaker technology, circuitry is known which will respond to electrical signals derived from detected heart activity signals and provide an output signal indicating detection of a signal exceeding a predetermined threshold level. Such circuitry is disclosed in German patent document P 32 32 478.2, corresponding to U.S. Pat. No. 4,516,579, as comprising a differentiator stage, peak detector stage, summing amplifier stage and comparator stage all connected in series. The input to the differentiator stage is coupled to receive signals derived from detected heart activity. One input to the comparator stage is coupled to a threshold voltage level Vref. When the summing amplifier input to the comparator stage exceeds the threshold voltage Vref, corresponding to the positive and negative slopes of a heart-derived signal differing by more than a certain amount, the output of the comparator stage goes high, thus indicating heart signal detection.

SUMMARY OF THE INVENTION

In brief, arrangements in accordance with the present invention comprise electrical circuitry for responding to a processed signal corresponding to sensed heart activity and developing an output which provides a measure of the extent by which the processed signal exceeds detector threshold level. In other words, these arrangements in accordance with the invention provide a measure of the sensing margin. This quantitative indication can be used to adjust threshold level and thereby increase or reduce sensing margin to an appropriate level for safe operation of the pacemaker. As an alternative, or in conjunction with adjustment of threshold level, the determination of sensing margin afforded by arrangements in accordance with the present invention may be used to adjust the gain in the programmable amplifier which is incorporated in the signal processor that is included in the circuitry ahead of the sensing detector.

The output of the signal processor, when heart activity is sensed, is a comparator signal at a level above a preset voltage reference or threshold. In one particular arrangement in accordance with the present invention, this comparator signal is utilized to control a timer counter which provides a measure of the time interval during which the comparator signal is active. In another particular arrangement in accordance with the present invention, the signal amplitude in the signal processor is measured to provide the indication of sensing margin.

BRIEF DESCRIPTION OF THE DRAWINGS

The above and other objects, features and advantages of the present invention will be more apparent from the following more particular description thereof presented in conjunction with the accompanying drawings, wherein.

DETAILED DESCRIPTION OF THE INVENTION

The following description is of the best presently contemplated mode of carrying out the invention. This description is not to be taken in a limiting sense but is made for the purpose of describing the general principles of the invention. The scope of the invention should be determined with reference to the appended claims.

Figure 1:
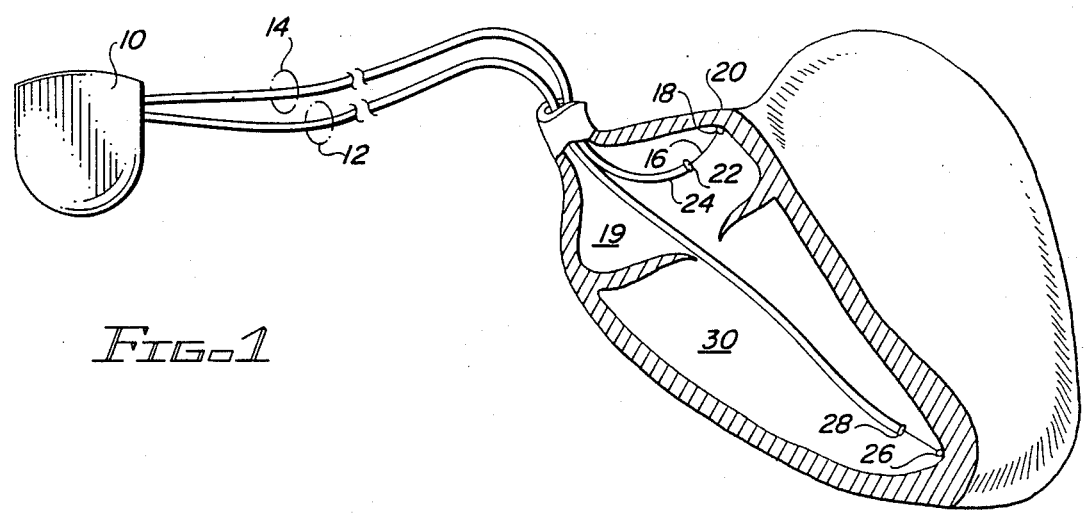
FIG. 1 is a schematic representation of a dual-chamber cardiac pacemaker shown implanted in association with a heart for pacing.

Referring now to FIG. 1, there is shown a simplified representation of one way that an implanted pacemaker 10 may make electrical contact with the heart. FIG. 1 depicts the use of two bipolar leads 12 and 14, each being directed into a separate chamber of the right heart. A bipolar lead comprises a single filar that includes two electrically insulated conductors. For example, the lead 14 includes a first conductor 16 that is electrically connected to a distal tip 18 of the lead. This distal tip is typically placed in a cavity of the right atrium 19 referred to as the atrial appendage 20. A known distance from the distal tip 18 an electrode ring 22 is electrically connected to the other conductor 24 of the bipolar lead 14. Similarly, a distal tip 26 and a conductive ring 28 are associated with the bipolar lead 12 that is placed in the apex of the right ventricle 30. The manner in which the leads 12 and 14 are inserted into the heart, as well as the manner in which the pacemaker 10 is implanted in the body of a patient, are well known in the art.

The diagram of FIG. 1 may be considered to represent a rate-responsive pacer operating in the VVI mode if the bipolar lead 14 with its associated distal tip 18 and electrode ring 22 is eliminated from the figure so that only the bipolar lead 12 is left with its tip and ring 26, 28 inserted in the ring ventricle 30, as shown in FIG. 1.

Figure 2:
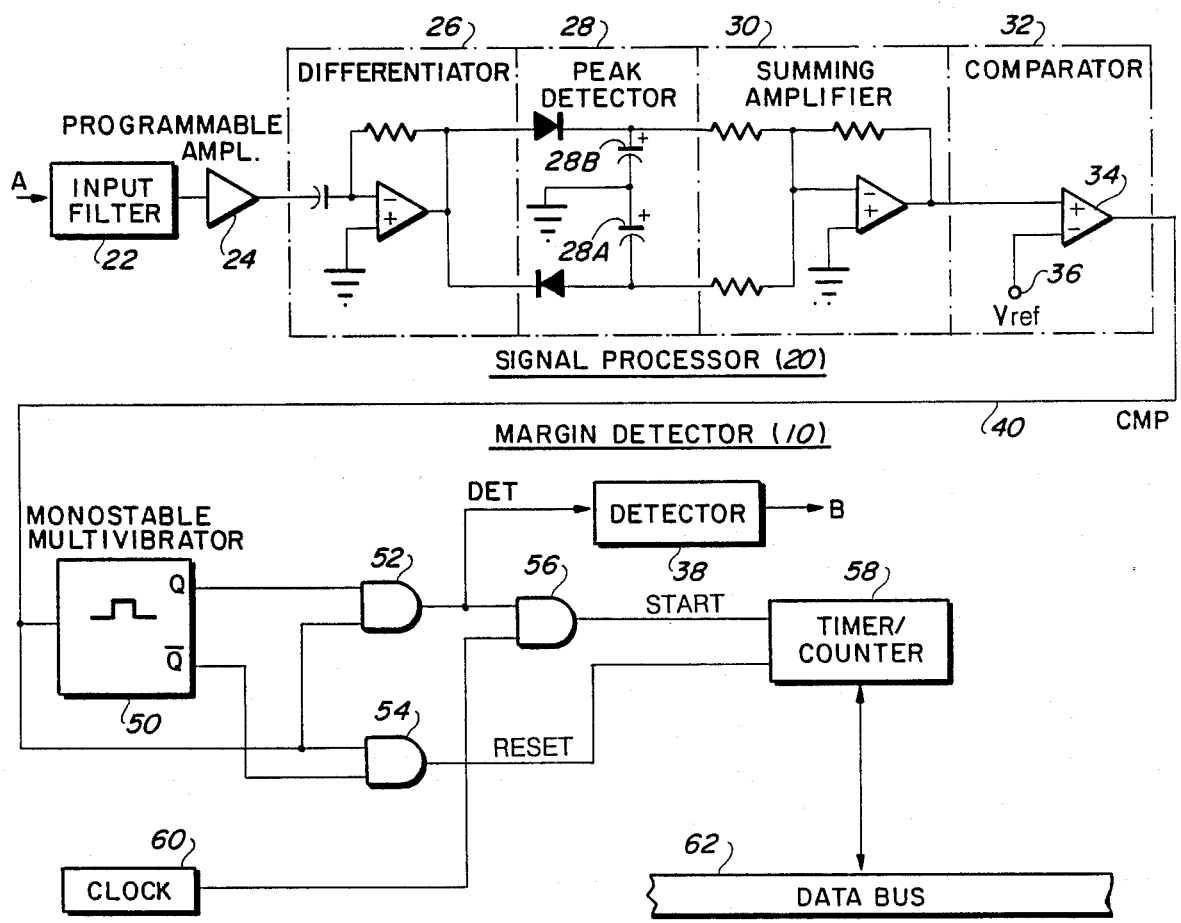
FIG. 2 is a schematic block diagram of one particular arrangement in accordance with the invention for incorporation in a pacemaker like that shown in FIG. 1.

FIG. 2 illustrates in schematic circuit form a margin detector 10 in accordance with one particular embodiment of the invention connected in circuit with a signal processor 20 of conventional form as used in implantable pacemakers such as the pacemaker 10 of FIG. 1. The specific signal processor 20 indicated in FIG. 2 is disclosed in German Pat. No. P 32 32478.2.

The signal processor 20 of FIG. 2 is shown comprising an input filter 22 for receiving heart signals at input A, as may be presented over one of the leads 12, 14 of FIG. 1. Following the input filter 22 is a programmable amplifier stage 24 which is connected in series with a differentiator stage 26, a peak detector stage 28, a summing amplifier 30 and comparator stage 32. The circuit components represented in these respective stages of the signal processor 20 are of conventional form and therefore need not be described in detail.

As is indicated in the block of the comparator stage 32, an amplifier 34 receives a processed signal from the summing amplifier 30 for comparison with a reference voltage, Vref, 36. This reference voltage 36 represents the threshold level of the sensing detector 38 in the margin detector 10. For processed signals from amplifier 30 which are less than Vref, the CMP output of comparator 32 is zero. If the input to comparator amplifier 34 exceeds Vref, the CMP output reverts to one (high level). As long as the comparator input signal exceeds the Vref level, the CMP output is held high. The timing of the CMP signal high level is an exponential function of peak signal level above Vref. The peak detector 28 capacitive elements are charged to a voltage level representing the peak voltage of the processed signal level. After such excitation, the comparator input voltage reaches its maximum and declines back to zero.

A pulse generator 50 is coupled to the CMP output 40 of the comparator amplifier 34. In the preferred embodiment, the pulse generator is a monostable multivibrator. The monostable multivibrator 50 is coupled to a number of gates 52, 54 and 56 which are connected to provide start and reset signals to a timer 58. Gate 56 is coupled to receive pulses from a clock 60 to control the counting of the timer 58. The sensing detector 38 is coupled to the DET output of gate 52 and provides an output signal B which may be used to initiate stimulation of heart activity with appropriate delay or to inhibit stimulation, depending on the pacemaker mode, when an appropriate DET input signal is applied from the output of the monostable multivibrator 50 through gate 52.

In the operation of the circuit of FIG. 2, the signal processor 20 is effective to suppress noise and other unwanted signals, in effect cleaning up the physiological signals from noise signals appearing at the input A. The input filter 22 is of a low pass type and is selected to eliminate signals with frequency content above the frequency for sensed heart signals. After filtering in the stage 22, the signal is amplified in the programmable gain amplifier 24 where the programmable sensitivity levels and polarity with respect to the input signal at A are developed. Within the signal processor proper, the negative and positive maximum slope of the signal is determined and compared. When the slope represented by the voltage across the capacitor 28A in the peak detector stage 28 exeeds the voltage across the adjacent capacitor 28B by a predetermined amount, related to the reference voltage 36, the comparator output CMP on line 40 is developed. This activates the monostable multivibrator 50. The monostable multivibrator 50 preferably is programmable to provide a predetermined delay before its active output is applied to the gate 52 to activate the detector 38 and generate sensing output signal B. In one configuration, the delay of the multivibrator 50 has been set at 40 milliseconds. It could be set or programmed over a range from 0 to 100 milliseconds. A longer delay results in better noise rejection.

The timer counter 58 of the margin detector 10 is clocked by input signals from the clock 60 when the DET signal is high. Timer 58 is reset on a CMP signal through gate 54 when the DET signal is low. The difference in the voltages across capacitors 28A and 28B is discharged by the resistive load of the summing amplifier 30, thereby developing a specified decay time period. The CMP signal is maintained high as long as this voltage difference is greater than the reference voltage 36. When the CMP signal returns low after the DET signal is established, the timer counter 58 stops counting and its terminal count is read out via the data bus 62. Thus the count applied to the data bus 62 is a measure of the sensing margin, being in this instance proportional to the time duration of the CMP signal, which in turn is related to the extent by which the voltage difference from the peak detector 28 exceeds the reference voltage 36.

Figure 3:
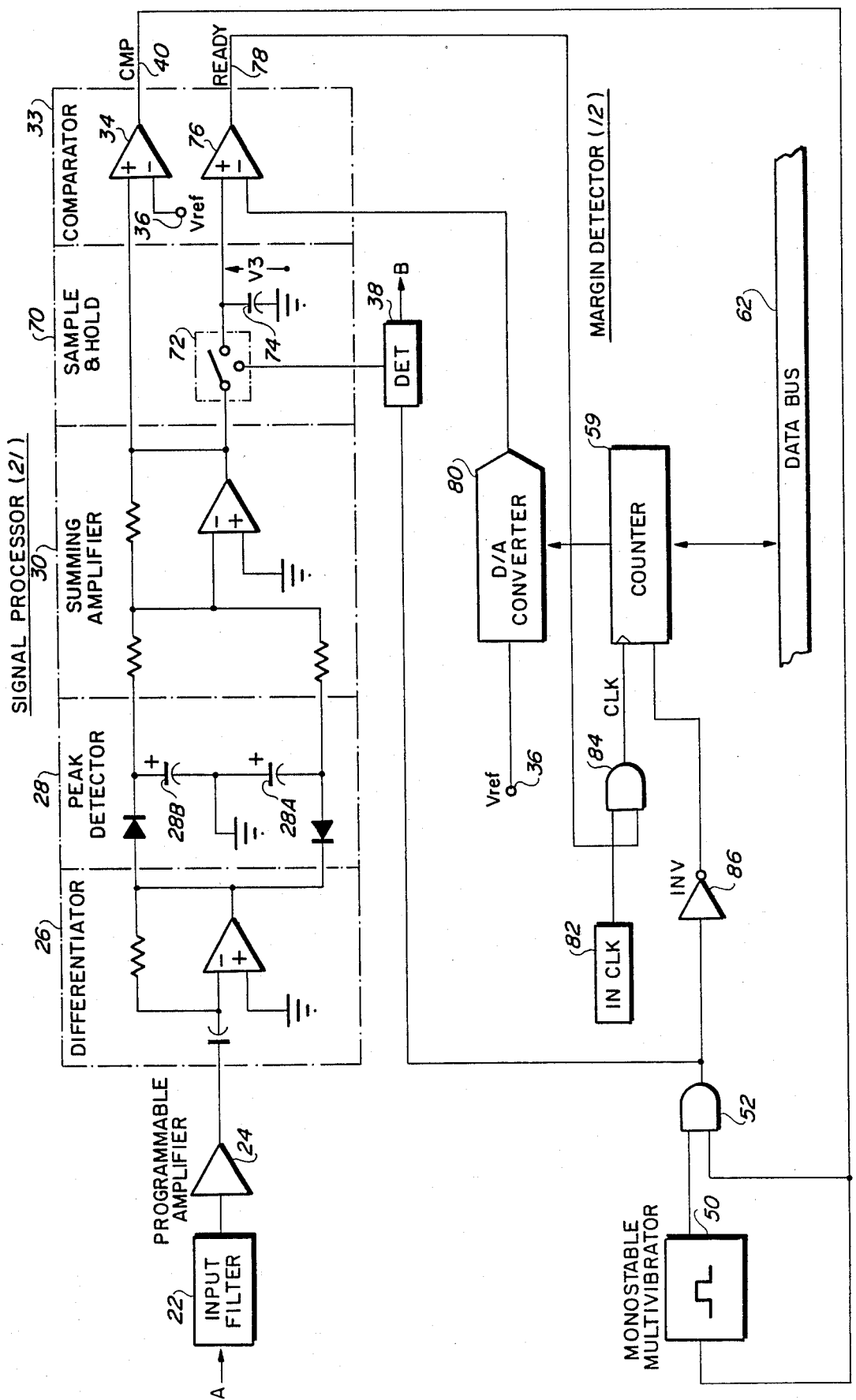
FIG. 3 is a schematic block diagram of a second particular arrangement in accordance with the present invention for inclusion in a pacemaker like that shown in FIG. 1.

The circuit of FIG. 3 is similar to that of FIG. 2 in the processing of heart signals in the manner in which corresponding signal B is developed to either stimulate or inhibit stimulation of the heart, depending upon the mode of operation of the associated pacemaker. The circuit of FIG. 3 comprises a signal processor 21 and a margin detector 12. The signal processor 21 is identical to the signal processor of FIG. 2 with the addition of a sample and hold circuit 70 at the output of the summing amplifier 30 and a second comparator amplifier 76 in comparator stage 33. Like elements in the circuit of FIG. 3 have been given the same reference numerals as those in the circuit of FIG. 2.

As described hereinabove, heart signals at A are processed through signal processor 21 to develop a CMP signal at the output 40 of comparator stage 34 when the voltage across capacitor 28A exceeds the voltage across the capacitor 28B in the peak detector stage 28 by the value of the reference voltage 36. This drives the monostable multivibrator 50 to force the DET line at the output of gate 52 high after an appropriate delay which is developed by programming the multivibrator 50.

In addition to the circuitry already described, the sample and hold stage 70 is shown comprising a switch circuit 72, controlled by the detector 38, and a capacitor 74 which holds the voltage $V_s$ from the summing amplifier 30 when the switch 72 is opened by the active output of the detector 38. The voltage $V_s$ is then applied to the second comparator 76, which also receives the output of a digital-to-analog (D/A) converter 80 coupled to the voltage reference stage 36. An IN clock stage 82 provides an input to a gate 84 which receives its other input from a READY line 78 at the output of the second comparator stage 76. An inverter stage 86 is coupled from the output of the gate 52 to the reset input of a counter 59 which is connected to receive clock pulses from the gate 84 when the READY line is not active. The counter 59 provides outputs to the D/A converter 80 and to the data bus 62.

In the operation of the circuit of FIG. 3, the sample and hold voltage $V_3$ follows the output of the summing amplifier 30, also applied to the comparator amplifier 34, as long as the DET signal is low. When the DET line goes high, the voltage level $V_3$ is frozen (held) and a D/A conversion started. The reset input to the counter 59 goes low and the counter begins counting under control of the pulses from the IN clock 82 through gate 84. Pulsing of the counter 59 continues until the voltage of the D/A converter 80 reaches $V_3$, and further clocking of the counter is stopped, at which time the analog output of the D/A converter is read via the bus as the sensed margin value.

The output to the data bus 62 in both the circuits of FIGS. 2 and 3 is in the form of a terminal count of a timer counter, thus presenting the measure of sensing margin in digital form. However, the measurement in the circuit of FIG. 2 is proportional to the time duration required for the output of the peak detector to decay to the level of the reference voltage, whereas in the circuit of FIG. 3 the count is a measure of the amplitude of the voltage from the peak detector sampled at the time that the sensing detector stage is activated. The measure of the sensing margin, as developed by either circuit arrangement in accordance with the present invention, may be used as an indication of the sensing margin, if desired, as well as to adjust the programmable sensing settings in order to provide an optimal and safe functional sensing operation of the pacemaker.

Although the present invention has been disclosed herein in the context of use in implantable cardiac pacemakers, it should be understood that the concepts of the invention are generally applicable to implantable electromedical devices other than pacemakers which utilize detection of a sensed event in controlling the provision of an electromedical stimulus. The present invention may find application in any implantable electromedical device which is dependent upon the sensing of physiological function or activity.

Although there have been developed particular arrangements of sensing margin detectors for pacemakers in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the annexed claims.

What is claimed is:

1. An implantable electromedical device for developing predetermined control signals in response to sensed physiological reactions comprising:
   signal processing means coupled to receive signals corresponding to electrophysiological activity and to develop processed signals in response thereto, the signal processing means including a sensing detector for developing output signals corresponding to said processed signals;
   means coupled to the sensing detector for establishing a threshold of response for said sensing detector, wherein the time duration of said output signal from said sensing detector corresponds to the time interval during which a processed signal exceeds said threshold level;
   sensing margin means for determining a sensing margin as the level of said processed signals relative to said threshold; and
   means for indicating the degree of difference between the processed signals and said threshold.

2. The device of claim 1 wherein the indicating means includes a counter responsive to signals from the sensing margin means for developing a terminal count which provides a digital measurement of sensing margin.

3. The device of claim 2 further including comparing means for providing a comparison output signal from the comparison of a processed signal with a predetermined reference voltage.

4. The device of claim 3 further including means for activating said counter from said comparison output signal for a time interval corresponding to the time that the processed signal exceeds said reference voltage.

5. The device of claim 4 wherein said signal processing means includes a combination of resistive and capacitive means for reducing the level of the processed signal over a predetermined decay interval.

6. The device of claim 3 further including variable delay means coupled to the comparing means to develop a control signal in response to the comparison output signal which is delayed therefrom by a predetermined time period.

7. The device of claim 6 wherein said variable delay means comprise a pulse generator having an adjustable delay interval.

8. The device of claim 7 wherein said pulse generator comprises a programmable monostable multivibrator having a delay interval which is selectable within a predetermined range.

9. The device of claim 6 wherein the signal processing means further include sample and hold circuitry for selectively storing a processed signal for an interval determined by said control signal.

10. The device of claim 9 wherein said sample and hold circuitry comprises a capacitor and a selectively interruptable switch means coupled to receive said processed signals, said capacitor being effected to maintain the level of an applied process signal upon the interruption of said switch means.

11. The device of claim 10 further including a second comparing means coupled to said capacitor, and means for applying a voltage signal to said second comparing means which corresponds to the duration of the active signal output of said first comparing means, said second comparing means being effective to develop an output signal representing the difference between the voltage across said capacitor and said applied voltage signal.

12. The device of claim 11 further including means for applying the output signal from said second comparing means to terminate the counting in said counter at a level signifying measured sensing margin.

13. The device of claim 12 further including means for applying the terminated count of said counter as an output measurement of sensing margin.

14. The device of claim 1 further including a programmable amplifier coupled in a series processing path for detected heart signals; and means for adjusting the gain of said programmable amplifier as determined by said sensing margin means.

15. The device of claim 1 wherein the device comprises an implantable cardiac pacemaker and the received signals correspond to heart activity.

16. The device of claim 15 wherein the indication means can be used to adjustably increase or decrease the sensitivity threshold level of said cardiac pacemaker.

17. An implantable device for controlling heart function comprising:

sensing means for detecting signals corresponding to heart activity;

signal processing means for developing processed signals corresponding to detected heart activity signals;

means for applying a predetermined threshold level to said processed signals in order to develop an output signal only in the event that a processed signal exceeds said threshold level, wherein the time duration of said output signal corresponds to the time interval during which a processed signal exceeds said threshold level; and sensing margin means responsive to said output signal for providing a measure of the extent by which a processed signal exceeds said threshold level, wherein said sensing margin means includes means for measuring the extent by which a processed signal exceeds said threshold level.

18. The device of claim 17 wherein said sensing margin means include means for measuring the duration of said output signal.

19. An implantable device for controlling heart function comprising:

sensing means for detecting signals corresponding to heart activity;

signal processing means for developing processed signals corresponding to detected heart activity signals, wherein said signal processing means includes a combination of resistors and capacitors in a charge decay circuit;

means for applying a predetermined threshold level to said processed signals in order to develop an output signal only in the event that a processed signal exceeds said threshold level; and sensing margin means responsive to said output signal for providing a measure of the extent by which a processed signal exceeds said threshold level, wherein said sensing margin means includes means for measuring the time during which the voltage of said charge decay circuit exceeds said threshold level.

20. An implantable device for controlling heart function comprising:

sensing means for detecting signals corresponding to heart activity;

signal processing means for developing processed signals corresponding to detected heart activity signals, wherein said signal processing means includes sample and hold circuit means coupled to hold a processed signal for a time interval proportional to the amplitude of said processed signal;

means for applying a predetermined threshold level to said processed signals in order to develop an output signal only in the event that a processed signal exceeds said threshold level; and sensing margin means responsive to said output signal for providing a measure of the extent by which a processed signal exceeds said threshold level.

* * * * *